US012714356B2

(12) United States Patent
Osorio

(10) Patent No.: US 12,714,356 B2
(45) **Date of Patent: *Aug. 25, 2026**

(54) EPILEPTIC SEIZURE PREVENTION OR TREATMENT VIA HEART RATE CLAMPING

(71) Applicant: Flint Hills Scientific, L.L.C., Lawrence, KS (US)

(72) Inventor: Ivan Osorio, Leawood, KS (US)

(73) Assignee: FLINT HILLS SCIENTIFIC, LLC, Lawrence, KS (US)

( * ) Notice: Subject to any disclaimer, the term of this patent is extended or adjusted under 35 U.S.C. 154(b) by 822 days.

This patent is subject to a terminal disclaimer.

(21) Appl. No.: 17/981,732

(22) Filed: Nov. 7, 2022

(65) Prior Publication Data

US 2023/0058287 A1 Feb. 23, 2023

Related U.S. Application Data

(60) Continuation of application No. 16/447,045, filed on Jun. 20, 2019, now Pat. No. 11,524,111, which is a (Continued)

(51) Int. Cl.

| | |
|---|---|
| ***A61B 5/00*** | (2006.01) |
| ***A61B 17/132*** | (2006.01) |
| ***A61F 7/00*** | (2006.01) |
| ***A61F 7/12*** | (2006.01) |
| ***A61M 5/172*** | (2006.01) |
| ***A61N 1/36*** | (2006.01) |

(Continued)

(52) U.S. Cl.
CPC ........ *A61B 5/4094* (2013.01); *A61B 17/1325* (2013.01); *A61F 7/007* (2013.01); *A61F 7/12* (2013.01); *A61M 5/1723* (2013.01); *A61N 1/36053* (2013.01); *A61N 1/36064* (2013.01); *A61F 2007/0056* (2013.01); *A61F 2007/0063* (2013.01); *A61F 2007/0075* (2013.01); *A61F 2007/0282* (2013.01); *A61F 7/10* (2013.01); *A61F 2007/126* (2013.01); *A61M 2230/30* (2013.01)

(58) Field of Classification Search
CPC ............ A61M 2230/30; A61M 5/1723; A61N 1/36064; A61B 5/4094
See application file for complete search history.

(56) References Cited

U.S. PATENT DOCUMENTS 10,363,362 B2 * 7/2019 Osorio ...................... A61F 7/12
11,524,111 B2 * 12/2022 Osorio ................ A61M 5/1723

* cited by examiner

*Primary Examiner* — William R Carpenter
(74) *Attorney, Agent, or Firm* — CF3; Stephen Eisenmann

(57) ABSTRACT

We report a method of treating an epileptic seizure in a patient, comprising: detecting said epileptic seizure, based on body data from said patient; and reducing a flow of blood to a brain of said patient in response to said detected seizure; wherein said reducing is effected by: increasing the parasympathetic input to said patient's heart, such as by electrically stimulating a parasympathetic nervous structure, applying cooling energy to a sympathetic nervous structure, or administering a cholinergic or a sympatho-blocking agent to said patient. We also report a medical device system configured to implement the method. We also report a non-transitory computer readable program storage unit encoded with instructions that, when executed by a computer, perform the method.

19 Claims, 4 Drawing Sheets

Related U.S. Application Data division of application No. 14/201,609, filed on Mar. 7, 2014, now Pat. No. 10,363,362.

(60) Provisional application No. 61/792,063, filed on Mar. 15, 2013, provisional application No. 61/805,085, filed on Mar. 25, 2013.

(51) Int. Cl.
*A61F 7/02* (2006.01)
*A61F 7/10* (2006.01)

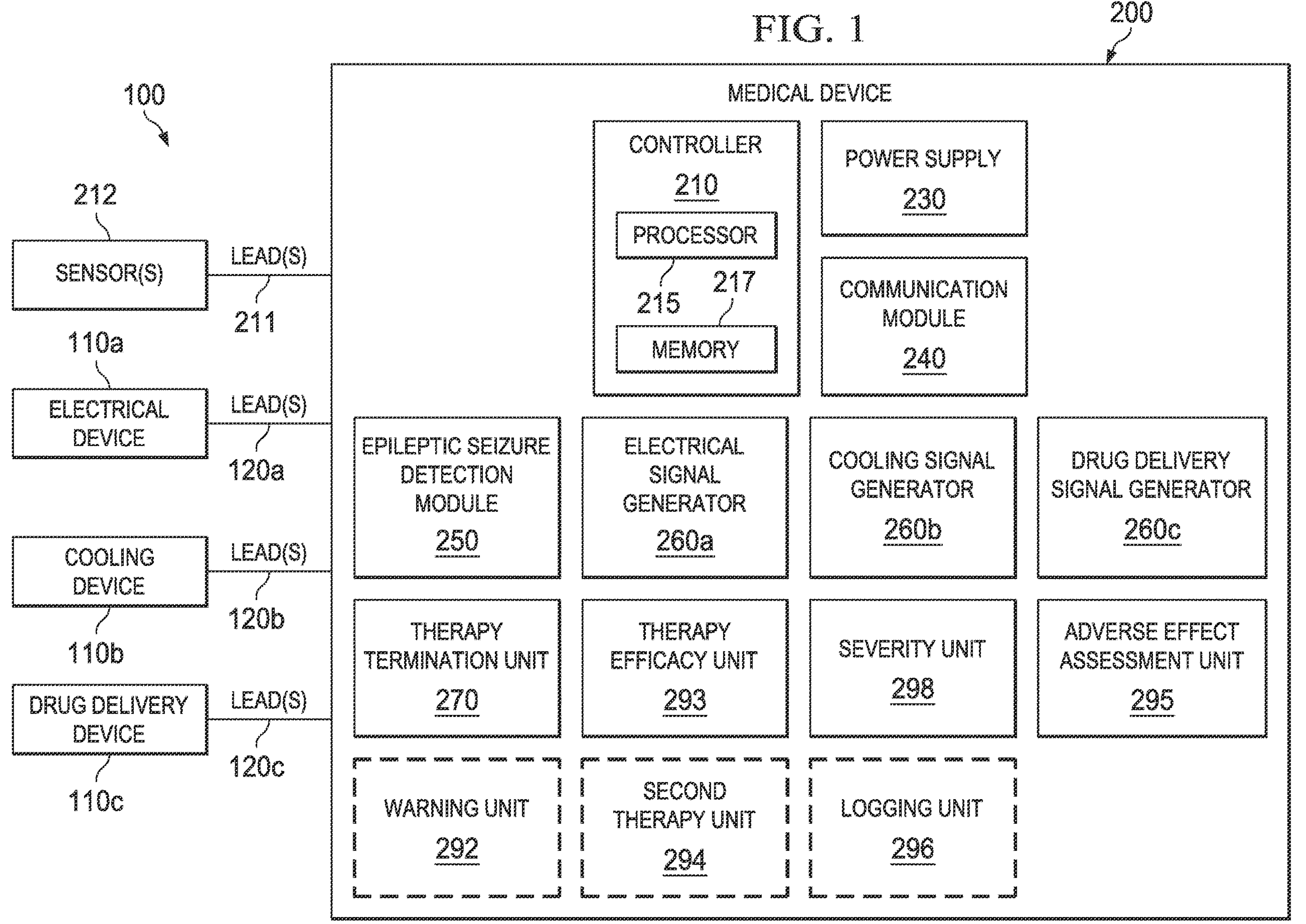
FIG. 1
200
MEDICAL DEVICE
CONTROLLER
210
PROCESSOR
215
217
MEMORY
POWER SUPPLY
230
COMMUNICATION MODULE
240
EPILEPTIC SEIZURE DETECTION MODULE
250
ELECTRICAL SIGNAL GENERATOR
260a
COOLING SIGNAL GENERATOR
260b
DRUG DELIVERY SIGNAL GENERATOR
260c
THERAPY TERMINATION UNIT
270
THERAPY EFFICACY UNIT
293
SEVERITY UNIT
298
ADVERSE EFFECT ASSESSMENT UNIT
295
WARNING UNIT
292
SECOND THERAPY UNIT
294
LOGGING UNIT
296
100
212
SENSOR(S)
LEAD(S)
211
110a
ELECTRICAL DEVICE
LEAD(S)
120a
COOLING DEVICE
LEAD(S)
120b
110b
DRUG DELIVERY DEVICE
LEAD(S)
120c
110c

EPILEPTIC SEIZURE PREVENTION OR TREATMENT VIA HEART RATE CLAMPING

This application is a continuation application of and claims priority to U.S. patent application Ser. No. 16/447,045 filed on Jun. 20, 2019, which is a divisional application of and claims priority to U.S. patent application Ser. No. 14/201,609 filed on Mar. 7, 2014 (Now U.S. Pat. No. 10,363,362) which claims priority to U.S. provisional patent applications 61/792,063, filed Mar. 15, 2013, and 61/805,085, filed Mar. 25, 2013, which are all hereby incorporated by their reference.

FIELD OF THE INVENTION

This disclosure relates to medical device systems and methods capable of treating epileptic seizures.

SUMMARY OF THE DISCLOSURE

In some embodiments, the present disclosure relates to a method of treating an epileptic seizure in a patient, comprising: detecting said epileptic seizure, based on body data from said patient; and reducing a flow of blood to a brain of said patient in response to said detected seizure; wherein said reducing is effected by increasing the parasympathetic input to the heart, by performing at least one of administering electrical stimulation to a parasympathetic nervous structure; delivering a cholinergic drug or a drug with sympatho-blocking actions; or applying a cooling to a sympathetic nervous structure.

In some embodiments, the present disclosure relates to a method of treating an epileptic seizure in a patient, comprising: detecting said epileptic seizure, based on body data from said patient; and decreasing parasympathetic input to the heart of said patient in response to said detected seizure; wherein said decreasing is performed by at least one of electrically stimulating a parasympathetic nervous structure, chemically stimulating a parasympathetic nervous structure, thermally blocking a sympathetic nervous structure, or chemically blocking a sympathetic nervous structure.

In some embodiments, the present disclosure relates to a medical device system, comprising: a therapy device selected from an electrical signal generator configured to apply electrical pulses to at least a portion of a parasympathetic structure innervating the heart of a patient, a cooling device configured to cool at least a portion of a sympathetic structure innervating the heart of said patient, or a drug delivery device configured to administer at least one of a cholinergic agent or a sympatho-blocking agent to said patient; and an epileptic seizure detection module configured to detect an occurrence of an epileptic seizure, based on body data from a patient; and a controller for controlling said therapy device to deliver a therapy in response to detecting the occurrence of an epileptic seizure or to stop or modify said therapy in response to an adverse event or a request from the patient to terminate said therapy.

In some embodiments, the present disclosure relates to a non-transitory computer readable program storage unit encoded with instructions that, when executed by a computer, perform a method as described above.

DESCRIPTION OF THE DRAWINGS

The disclosure may be understood by reference to the following description taken in conjunction with the accompanying drawings, in which like reference numerals identify like elements, and in which:

FIG. 1 shows a schematic diagram of a medical device system, in accordance with some embodiments of the present disclosure;

Figure 2A:
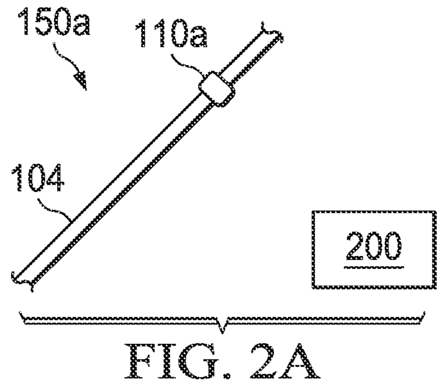
FIG. 2A shows a schematic diagram of an implanted medical device system, in accordance with some embodiments of the present disclosure.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION OF SPECIFIC EMBODIMENTS

Illustrative embodiments of the disclosure are described herein. For clarity, not all features of an actual implementation are described. In the development of any actual embodiment, numerous implementation-specific decisions must be made to achieve design-specific goals, which will vary from one implementation to another. Such a development effort, while possibly complex and time-consuming, would nevertheless be a routine undertaking for persons of ordinary skill in the art having the benefit of this disclosure.

In some embodiments, this disclosure relates to a treatment for preventing, blocking, or attenuating an epileptic seizure in a patient by controlling blood flow to the patient's brain. The blood flow to the brain may be controlled through either reducing the patient's heart rate or preventing an increase in heart rate associated with a seizure by exerting a negative chronotropic or inotropic action on the patient's heart. Alternatively or in addition to heart rate, blood pressure is also susceptible to such actions. A resulting reduction or prevention of an ictal increase in blood pressure may also prevent, block, or attenuate an epileptic seizure.

A case example to illuminate some of the concepts used herein may be as follows: The heart rate (HR) of a patient before a seizure is 80 beats per minute (bpm) and it reaches a peak value of 130 bpm during the seizure. Negative chronotropic or inotropic actions may be: a) Maintain the HR at 80 pm (the pre-ictal value) until there are beneficial or adverse effects; b) Prevent a full increase in HR: Keep heart at 90 bpm (40 bpm below its peak value) until there are beneficial or adverse effects; c) Decrease the HR to and maintain it at 70 bpm (10 bpm below pre-ictal value) until there are beneficial or adverse effects.

Embodiments disclosed herein provide for reducing the flow of blood to the brain in response to anticipating or detecting a seizure. Upon anticipating or detecting a seizure based upon body data of a patient, blood flow to the patient's epileptogenic tissue or network(s) may be reduced. One or more of a plurality of steps may be taken to reduce the flow of blood to the patient's brain, e.g., activating chemically or electrically a parasympathetic nervous structures (e.g., vagus nerve), decreasing sympathetic activity via electrical, chemical (e.g., sympatho-blocking drugs), or cooling means, etc.

In some embodiments, reducing the flow of blood to the brain may involve delivery of a stimulation signal (whether electrical, mechanical, magnetic, electro-magnetic, photonic, acoustic, cognitive, and/or chemical in nature) to a cranial nerve and/or another nervous tissue structure.

Embodiments disclosed herein may provide for selective therapeutic reduction in the supply of energy substrates (via a reduction in arterial blood flow) to epileptogenic or pro-epileptogenic structures to prevent the occurrence of seizures or to block them if they have started, without impairing the function of non-epileptogenic or non-pro-epileptogenic networks. An equal or similar reduction in blood flow (or prevention of increased blood flow) to both (i) epileptogenic or epileptotonic networks and (ii) brain regions not involved in seizure generation/maintenance will have a greater impact on the epileptogenic or epileptotonic networks, given their much greater demands for metabolic substrates relative to non-epileptogenic/epileptotonic brain tissue. Thus, the final effect of this reduction in blood flow to the brain as a whole is to cause a relative non-cytopathological transient "starvation" of energy substrate to the epileptogenic or epileptotonic networks, with the final effect of blocking, abating, etc. the seizure.

Although decreasing blood flow to the brain is one particular embodiment of the present disclosure, other techniques, devices, or agents to provide controlled constraint on energy delivery to the epileptogenic or epileptotonic brain region(s) may be used.

Some embodiments of the present disclosure relate to a medical device system, as shown in FIG. 1. The medical device system 100 may comprise a medical device 200, sensor(s) 212, and lead(s) 211 coupling the sensor(s) 212 to the medical device 200. In various embodiments, the medical device 200 may be implantable within a patient's body, may be external to a patient's body (e.g., part of a patch affixed to the patient's skin or in a housing suitable for wearing in a pocket, on a lanyard around the neck, etc.), or may be remote from the patient's body.

In one embodiment, sensor(s) 212 may each be configured to collect data from a patient from whom a pathologic brain state, such as an epileptic seizure, may be detected.

More information regarding detecting an epileptic event from cardiac data, as well as information regarding measures of central tendency that can be determined from time series of body data, may be found in other patent applications assigned to Flint Hills Scientific, LLC or Cyberonics, Inc., such as, U.S. Ser. No. 12/770,562, filed Apr. 29, 2010; U.S. Ser. No. 12/771,727, filed Apr. 30, 2010; U.S. Ser. No. 12/771,783, filed Apr. 30, 2010; U.S. Ser. No. 12/884,051, filed Sep. 16, 2010; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598,339, filed Aug. 29, 2012. Each of the patent applications identified in this paragraph is hereby incorporated herein by reference.

More information regarding detecting an epileptic event from multiple body data types, and examples of such body data types, may be found in other patent applications assigned to Flint Hills Scientific, LLC or Cyberonics, Inc., such as, U.S. Ser. No. 12/896,525, filed Oct. 1, 2010, now U.S. Pat. No. 8,337,404, issued Dec. 25, 2012; U.S. Ser. No. 13/098,262, filed Apr. 29, 2011; U.S. Ser. No. 13/288,886, filed Nov. 3, 2011; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598,339, filed Aug. 29, 2012. Each of the patent applications identified in this paragraph is hereby incorporated herein by reference.

More information regarding the detection of abnormal brain activity, such as seizures, identifying brain locations susceptible to spread of the abnormal brain activity, and treating the susceptible brain locations may be found in other patent applications assigned to Flint Hills Scientific, LLC or Cyberonics, Inc., such as, U.S. Ser. No. 13/449,166, filed Apr. 17, 2012. Any patent application identified in this paragraph is hereby incorporated herein by reference.

More information regarding automated assessments of therapies may be found in other patent applications assigned to Flint Hills Scientific, LLC or Cyberonics, Inc., such as, U.S. Ser. No. 12/729,093, filed Mar. 22, 2010; U.S. Ser. No. 13/280,178, filed Oct. 24, 2011; U.S. Ser. No. 13/308,913, filed Dec. 1, 2011; and U.S. Ser. No. 13/472,365, filed May 15, 2012. Each of the patent applications identified in this paragraph is hereby incorporated herein by reference.

More information regarding the detection of brain or body activity using sensors implanted in proximity to the base of the skull may be found in other patent applications assigned to Flint Hills Scientific, LLC or Cyberonics, Inc., such as, U.S. Ser. No. 13/678,339, filed Nov. 15, 2012. Any patent application identified in this paragraph is hereby incorporated herein by reference.

Various components of the medical device 200, such as controller 210, processor 215, memory 217, power supply 230, communication unit 240, warning unit 292, second therapy unit 294, logging unit 296, and severity unit 298 have been described in other patent applications assigned to Flint Hills Scientific, LLC or Cyberonics, Inc., such as those incorporated by reference, supra.

As shown in FIG. 1, the medical device system 100 may comprise at least one of an electrical device 110*a* configured to deliver electrical pulses to a parasympathetic or to a sympathetic nervous structure of a patient, a cooling device 110*b* configured to cool at least a portion a sympathetic nervous structure innervating the heart, or a drug delivery device 110*c* configured to administer at least one of a cholinergic or a sympatho-blocking drug to a structure innervating the heart to the patient via injection into the blood stream or directly into a parasympathetic nervous structure or a sympathetic nervous structure. In other words, the drug delivery device 110*c* may deliver the drug systemically or locally.

In some embodiments, the electrical pulse generator 110*a* may be one of several models available commercially (e.g., Cyberonics devices). Generally, it is desirable for the degree of induced bradycardia to not reduce blood flow to the brain below a level that will disrupt the normal functions of non-epileptogenic or non-ictiogenic structures. Because an epileptic seizure is a highly energy consuming event (several fold compared to non-ictal activity), a "small" reduction in blood flow to the patient's brain, will have a much greater (e.g., differential) impact on the epileptogenic or pro-epileptogenic zones, than on brain regions not engaged in this activity. A reduction, or a prevention of an ictal increase, in blood flow to the brain will "starve" (e.g., "consumptive non injurious hypoxia") the epileptogenic or pro-epileptogenic zones of energy substrates (oxygen and glucose) while allowing parts of the brain regions free from seizures to function normally, since their metabolic demands are much lower than those of epileptogenic tissue. Partial and safe (for tissue integrity/vitality and preservation of normal neurologic functions) decreases in blood low may be sufficient to deprive and/or transiently relatively "deplete" the epileptogenic region of energy substrates required to support seizures, a metabolically highly costly phenomenon, without disrupting normal functions of brain regions not engulfed by seizures.

As shown in FIG. 2A, electrical device 110*a* may be implanted to a portion 104 of a parasympathetic nervous structure.

In some embodiments, the cooling device 110*b* may be a thermoelectric device (e.g., a Peltier cooler) appropriately modified to avoid injury to the nerve or ganglion or to neighboring structures by the heat generated on one side of said device. A device capable of containing a flowing refrigerant (e.g., cold saline) system may be also used. Regardless of the type of the cooling device 110*b*, it may be configured to cool a portion of a sympathetic nervous structure innervating the heart (e.g., a sympathetic nerve or sympathetic ganglion) to one temperature, or allow selection of one of multiple temperatures to which the portion of those structures may be cooled. Generally, the cooling temperature should be kept above 6-10° C. to minimize the probability of freeze injuries to tissue. Cooling of a nerve or a ganglion decreases its activity.

Figure 2B:
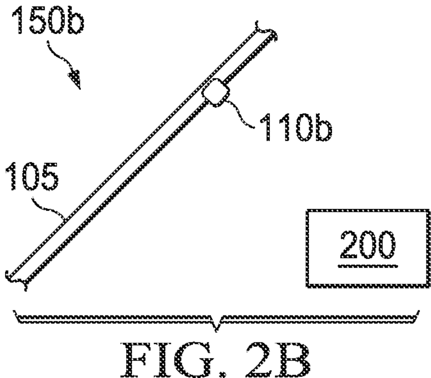
FIG. 2B shows a schematic diagram of an implanted medical device system, in accordance with some embodiments of the present disclosure.

As shown in FIG. 2B, cooling device 110*b* (in one embodiment, a thermoelectric device) may be implanted to a portion 105 of a sympathetic nervous structure innervating the heart.

The drug delivery 110*c* may be configured to deliver any appropriate cholinergic or sympatho-blocking agent systemically or locally to structures innervating the heart. The drug delivery device 110*c* may comprise at least one drug reservoir, and appropriate perfusing, or pumping and metering apparatus.

Figure 2C:
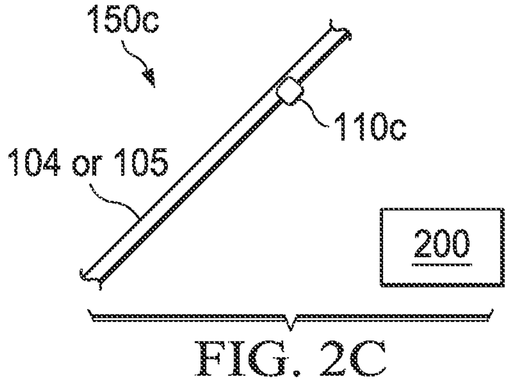
FIG. 2C shows a schematic diagram of an implanted medical device system, in accordance with some embodiments of the present disclosure.

As shown in FIG. 2C, drug delivery device 110*c* may be implanted to a portion 104 of a parasympathetic nervous structure or a portion 105 of a sympathetic nervous structure.

The medical device 200 may comprise a controller 210 configured to direct the operations of other elements of the medical device 200 and the medical device system 100.

The medical device 200 may comprise an epileptic seizure detection module 250 configured to detect an occurrence of an epileptic seizure and determine its severity, based on body data from a patient, such as that collected via sensor(s) 212.

The medical device 200 may comprise at least one therapy device selected from a electrical signal generator 260*a* configured to deliver electrical pulses to a parasympathetic nervous structure, e.g., a vagus nerve or a structure related to said nerve, a cooling signal generator 260*b* configured to apply the cooling using the cooling device, or a drug delivery signal generator 260*c* configured to apply the cholinergic or sympatho-blocking agent using the drug delivery device. Regardless of the type of therapy, therapy device 260*c*-260*c* may be configured to receive an indication of an epileptic seizure from epileptic seizure detection module 250 and direct the application of electrical signals, cooling, or drugs/chemicals via the corresponding device 110*a*-110*c*. Drugs or chemicals may be administered systemically (e.g., orally, intravenously, rectally or through inhalation) or locally (e.g., to the nerve or ganglion of interest).

The medical device 200 may comprise one, two, or all three therapy devices 260*a*-260*c* and corresponding devices 110*a*-110*c*. In some embodiments, the medical device system 100 comprises electrical device 110*a* and the therapy device comprises the electrical signal generator 260*a*. In some embodiments, the medical device system 100 comprises cooling device 110*b* and the therapy device comprises cooling signal generator 260*b*. In some embodiments, the medical device system 100 comprises a drug delivery agent device 110*c* and the therapy device comprises drug signal generator 260*c*. A device capable of two or more of administering an electrical signal, applying a cooling, and delivering a drug may be used for prevention or treatment of seizures.

In some embodiments, the medical device 200 may further comprise a therapy termination unit 270 configured to direct the therapy unit(s) 260*a*-260*c* to stop the therapy in response to at least one directive to stop therapy based on one or more of a) prevention or termination of the seizure as determined based on the analyses of body signals such as may be determined by epileptic seizure detection module 250, therapy efficacy unit 293, and/or severity unit 298); b) an increase in power in the 0-4 Hz frequency band in at least one brain region (such as may be determined by epileptic seizure detection module 250, therapy efficacy unit 293, adverse effect assessment unit 295, and/or severity unit 298); c) a decrease in power in all frequency bands in at least one brain region (such as may be determined by epileptic seizure detection module 250, therapy efficacy unit 293, adverse effect assessment unit 295, and/or severity unit 298); d) an impairment of a neurological function in at least one brain region (such as may be determined by therapy efficacy unit 293, adverse effect assessment unit 295, and/or severity unit 298); e) a change in antigravitatory muscle tone outside a normal range (such as may be determined by adverse effect assessment unit 295, based on signals provided by an appropriate sensor 212); f) any impairment in neurologic function or g) an input from a patient or care-giver requesting said therapy be terminated (such as may be received via communication module 240). In case a), upon termination of the seizure, further therapy may no longer be needed. In cases b)-g), the therapy may lack efficacy and/or give rise to adverse effects, either or both of which suggest the therapy is inadequate and another therapy may be delivered, either by another therapy device 260*a*-260*c* or a second therapy unit 294. In case g), the patient may perceive a lack of efficacy and/or an adverse effect that is not identified, or the magnitude of which is not fully identified, by a unit of the medical device system.

When stopping therapy, the therapy device 260*a*-260*c* may be configured in one embodiment to gradually reduce electrical stimulation, gradually rewarm, or gradually reduce delivery of the cholinergic or sympatho-blocking agent.

If included in the medical device 200, the second therapy unit 294 may provide any therapy known to the person of ordinary skill and/or disclosed by the Flint Hills and/or Cyberonics patent applications incorporated by reference. In a particular embodiment, the second therapy unit may be a vagus nerve stimulator, such as one commercially available from Cyberonics, Inc.

In some embodiments, units 250-298 may be components of the medical device 200. In some embodiments, one or more of units 250-298 may be external to the medical device 200, such as in an implantable device, an external device, a remote device, etc.

Figure 3:
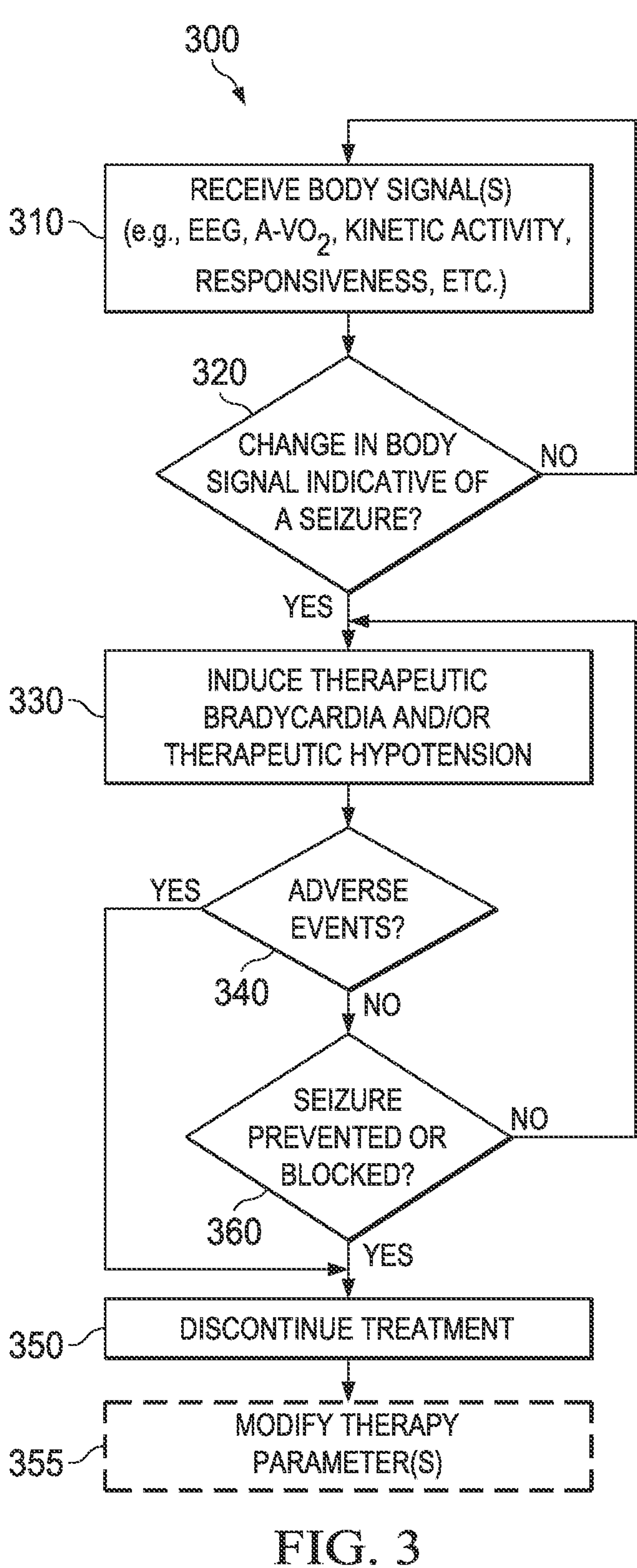
FIG. 3 shows a flowchart depiction of a method, according to some embodiments of the present disclosure.

FIG. 3 shows a flowchart representation of a method 300 of treating an epileptic seizure in a patient, comprising receiving at 310 (*a*) body signal(s) (e.g., an electroencephalography (EEG) signal, a cardiac signal, an arterial-venous blood oxygen difference (A-$VO_2$) signal, a kinetic activity signal, a responsiveness signal, etc.). If a change in the body signal(s), as determined at 320, indicates a seizure, then therapeutic bradycardia and/or therapeutic hypotension may be induced at 330. (If no change indicative of a seizure is detected at 320, then flow may return to receiving body signal(s) at 310).

Therapeutic hypotension, as used herein, refers to hypotension relative to an ictal maximum blood pressure and/or a preictal average, median, or mean blood pressure. "Hypotension" may refer to reducing the patient's blood pressure or preventing an ictal increase in blood pressure.

If the therapeutic bradycardia and/or therapeutic hypotension gives rise to one or more adverse events, as determined at 340, then the bradycardic/hypotensive treatment may be discontinued (at 350) or reverted using appropriate means. (One or more parameters of the therapy may be modified at 355, if desired). If the therapeutic bradycardia and/or therapeutic hypotension has no adverse events, then a determination may be made at 360 as to whether or not the seizure is prevented, blocked, or otherwise mitigated in whole or in part. If the seizure is not prevented, blocked, etc., then therapeutic bradycardia and/or therapeutic hypotension may continue unchanged or following modifications (at 330). If the seizure is prevented, blocked, etc., then the bradycardic/hypotensive treatment may be discontinued (at 350).

Figure 4:
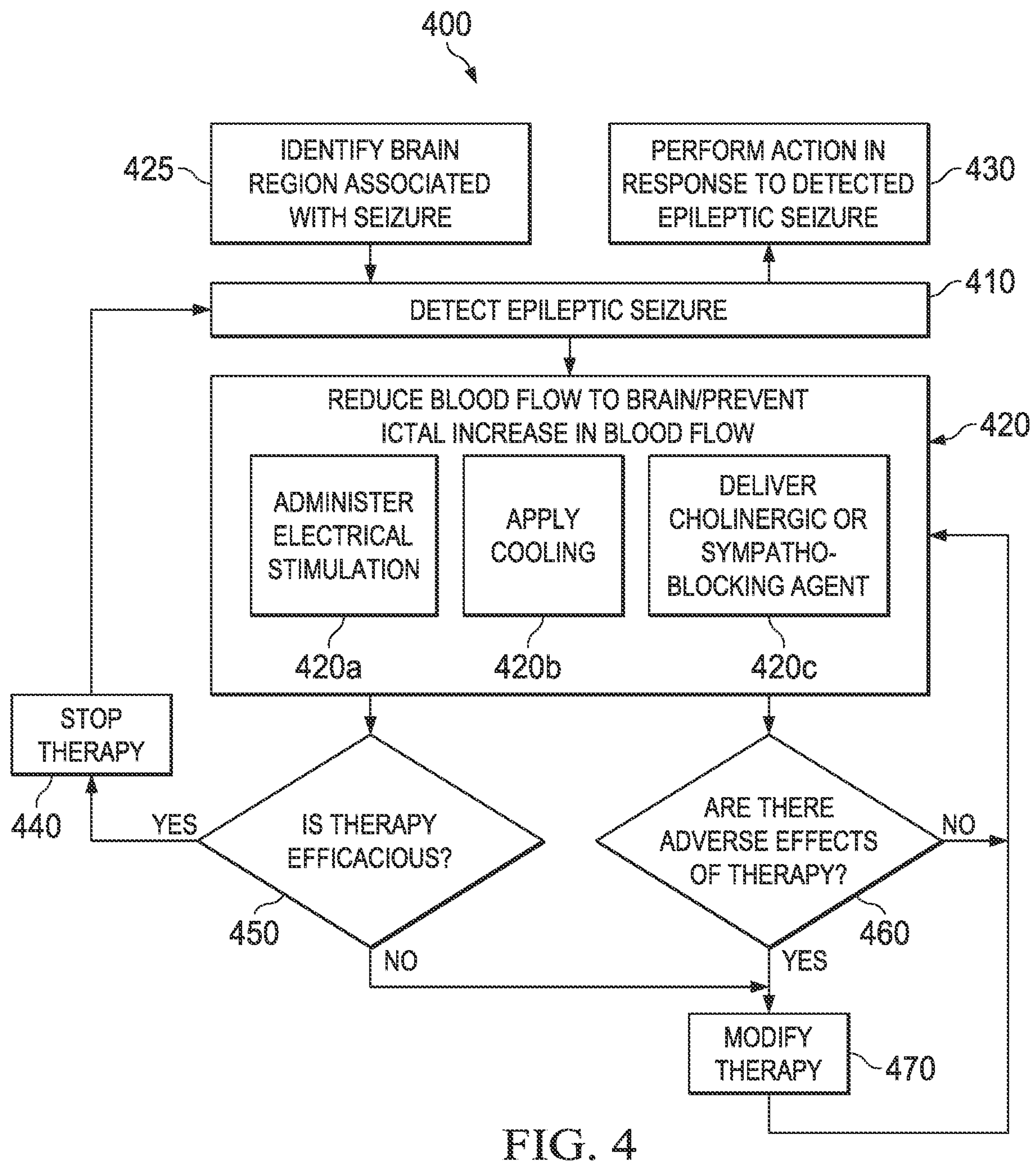
FIG. 4 shows a flowchart depiction of a method, according to some embodiments of the present disclosure.

As shown in FIG. 4, a method 400 relates to detecting at 410 an epileptic seizure, based on body data from the patient. In response, the method 400 may further comprise reducing at 420 a flow of blood (or preventing an ictal increase in the flow of blood) to a brain of the patient in response to the detected seizure, wherein the reducing is effected by at least one of: administering at 420*a* an electrical stimulation to a parasympathetic nerve structure, applying at 420*b* a cooling, or delivering at 420*c* a cholinergic or a sympatho-blocking agent for the purpose of reducing heart rate (negative chronotropic effect), preventing an ictal increase in heart rate, reducing stroke volume (negative inotropic effect), and/or preventing an ictal increase in stroke volume, to reduce blood flow to a patient's brain, said reduction having a differential effect in epileptogenic and non-epileptogenic networks. In some embodiments, the method 400 may include perform an action in response to the detected seizure (at 430). The action performed at 430 may comprise providing a second therapy (e.g., electrical therapy, chemical therapy, etc.) for attenuating the seizure and/or its effects. Alternatively or in addition, the action performed at 430 may also comprise logging the seizures, the effects of the therapy, the environmental circumstances associated with the seizure, and/or the actions taken in response to the seizure. Moreover, a warning may be provided in response to the seizure, wherein the warning may comprise providing a warning signal to the patient, to a healthcare personal, and/or to any designee. The warning may be audible, mechanical, and/or electronic (e.g., electrical signal, electronic communication, such as a telephone message, text messages, voicemail, email, and/or the like).

In some embodiments, the method 400 may further comprise identifying at 425 a brain region associated with the seizure. Identifying at 425 may be of an epileptogenic or pro-epileptogenic brain region. In some embodiments, identifying at 425 may be performed as part of an initial patient workup, e.g., through the use of electroencephalography or other appropriate imaging techniques, a brain region found to be epileptogenic or proepileptogenic in a major fraction of the patient's seizures may be identified. Information gained by the identifying at 425 may be useful in placing sensing electrodes and/or analyzing data used in the detecting at 410 of the epileptic seizure.

In some embodiments, the method 400 may further comprise stopping 440 the therapy in response to a determination at 450 that the therapy is efficacious. In other words, if the therapy prevents, reduces, blocks, or attenuates the seizure, further therapy may not be needed.

The determination at 450 may find that the therapy lacks efficacy. If so, the method 400 may further comprise modifying the therapy at 470. Modifying at 470 may comprise changing one or more parameters of the therapy (e.g., dosage, delivery rate, etc. of a drug; amplitude, pulse width, interpulse interval, duty cycle, etc. of an electrical stimulation; etc.), the anatomical target of the therapy (e.g., from one of electrical stimulation of a parasympathetic structure, cooling a sympathetic structure, drug delivery to a parasympathetic structure, or drug delivery to a sympathetic structure to another), the modality of the therapy (e.g., from electrical to cooling), the number of therapy modalities and/or targets (e.g., continuing electrical stimulation of a parasympathetic structure and beginning cooling of a sympathetic structure) or the like. Upon a modification of the therapy at 470, blood flow may be reduced, or an ictal increase in blood flow may be prevented, at 420.

In one embodiment, stopping (block 440) or modifying (block 450) a therapy may comprise at least one of a) a termination of the seizure; b) an increase in power in the 0-4 Hz frequency band in at least one brain region; c) a decrease in power in all frequency bands in at least one brain region; d) an impairment of a neurological function in at least one brain region; e) a change in antigravitatory muscle tone outside a normal range; f) an input from a patient requesting said therapy be terminated or modified; g) an unsafe drop in blood pressure; h) a drop in heart rate or blood pressure greater than that which was pre-specified, or i) an overly prolonged or intense prevention of increases in heart rate or blood pressure. In other words, therapy may be stopped at 440 if the seizure terminates, the therapy lacks efficacy, and/or the therapy gives rise to an adverse effect.

In one embodiment, the patient's heart rate is decreased to a minimum tolerable or safe rate consistent with the state of the patient. The minimum tolerable rate may differ, for example, depending upon whether the patient is: a) standing still; b) sitting down; or c) in a recumbent position. The maximum tolerable decrease (i.e., the minimum tolerable heart rate) may be determined based upon a variety of inputs including the patient's report (e.g., I feel dizzy, my vision is dimming, etc.); clinical testing (e.g., neurological exam); electrophysiological testing (e.g., EEG), or imaging testing (e.g., PET scan, fMRI). In one embodiment, the level of responsiveness or awareness, reaction time, electrocortical signals (spontaneous or evoked), blood pressure, arterial oxygen saturation, postural tone, etc., may be used to determine in an objective manner and with high degree of sensitivity the maximum tolerable reduction in heart rate with the patient in any body position or while engaged in certain physical or mental activities.

In some embodiments, a patient state module in the medical device may determine an acceptable (e.g., safe or tolerable) minimum heart rate for the patient to abort, attenuate, or reduce the likelihood of a seizure based on one or more of the foregoing data. The patient state module may incorporate one or more body data algorithms to ensure that the patient's heart rate is not reduced such that adverse effects (e.g., syncope, transient ischemic attack or stroke) associated with the induced bradycardia/blood pressure drop or prevented ictal increase in same, would occur. In one embodiment, the patient state module may receive input from a patient to terminate the therapy if therapy delivery may be associated with adverse events (e.g., dizziness, visual impairment, a sense of weakness, etc.). In one embodiment, the state module may also terminate the therapy if it does not receive an input from the patient for the therapy to be continued. This may protect the patient from adverse effects that may impair responsiveness, awareness or motor control.

Increases in heart rate associated with epileptic seizures may depend upon the patient's activity level or state at the time of the seizure, and may be mediated by neurogenic or exertional/metabolic factors, or both. For example, a maximum increase may occur in reference to a resting patient (e.g., resting heart rate at the time of seizure onset: 55 bpm; maximal ictal HR: 140 bpm; absolute increase=95 bpm). Less marked HR increases may occur when the heart rate is above a resting value when the seizure occurs, such as when the patient is active (e.g., the patient is walking and heart rate is 80 bpm; seizure increases HR to 120 bpm; relative increase=40 bpm). Less significant increases may also be attributable to less severe seizures, which may have a reduced neuropathological effect on the heart rate compared to more severe seizures.

Neurogenic increases are those caused by ictal excitation (or inhibition) of central autonomic network structures. A seizure manifesting with motionlessness and tachycardia is an example of neurogenic changes in heart rate. Neurogenic plus exertional/metabolic changes occur with seizures manifesting with increased motor activity, the extreme case being generalized tonic-clonic seizures during which hypoxemia, hypercapnia, and lactic acidosis contribute to increases in heart rate. In some embodiments, seizures manifesting with tachycardia are treated with induced bradycardia or hypotension, the magnitude of which may depend on the patient state (e.g., resting or active) at seizure onset, and/or the neurogenic and exertional/metabolic components of the seizure. In one embodiment, the heart rate during a seizure is maintained at an immediately pre-ictal value (e.g., a baseline pre-ictal HR).

In some embodiments, the magnitude of therapeutically induced bradycardia is determined by the increase in heart rate caused by the seizure. For example, if the seizure increases the heart rate by 30 bpm, actions may be taken to prevent the increase in heart rate by the same quantity (30 bpm). Since for a given patient, the increase in heart rate caused by a seizure may depend on multiple factors (such as its severity, the time of day, the patient's level of consciousness, and physical or cognitive activity), the magnitude of therapeutically induced bradycardia may be determined by these factors and may be a variable. Electrocortical signals, oxygen consumption by the brain (determined based on arterio-venous $O_2$ differences such as between a carotid artery and its ipsilateral jugular vein) or by the body (in the case of a convulsion), level of responsiveness, level of awareness, kinetic activity, postural tone, etc. may be used as feedback signal(s) to control the heart rate in therapeutically induced bradycardia in response to a seizure manifesting with tachycardia. In one embodiment, one or more parameters of an electrical signal (such as frequency, current intensity, pulse duration, signal on-time, signal off-time, or the site(s) to which the signal is delivered), may be automatically controlled (using a linear or non-linear function without or with a delay) by the magnitude or rate of change in heart rate associated with the seizure. In some embodiments, the occurrence of any adverse effect resulting from the induced relative bradycardia, or relative hypotension, may be mitigated by immediate termination of the responsive electrical stimulation or by administrations of a drug with sympathomimetic or with anticholinergic actions. A similar approach may be used for drugs (cholinergic or sympatho-blocking) or for cooling of sympathetic nervous structures used to induce relative bradycardia or relative hypotension. In the case of drugs, the type, dose, rate or route of delivery and site of delivery may be controlled based on the magnitude, rate and duration of change of body signals caused by a seizure. For cooling, the temperature, rate and site to which it is applied will be controlled similarly. As used herein, terms "relative bradycardia" and "relative hypotension" may not conform to the common clinical definitions. In some embodiments, "relative bradycardia" may not involve actually reducing HR to a low level, but maintaining or preserving a heart rate at a pre-ictal level. If the heart rate during an epileptic seizures typically increases by 30 bpm (e.g., from 80 immediately before seizure onset to 110 bpm) and said the patient's actual heart rate is maintained at 80 bpm or even decreased to 70 bpm, this is inducing relative bradycardia as used herein, even though the actual heart rate change is minimal or zero. Another meaning of the term relative bradycardia or hypotension is that which does not cause adverse events.

In yet other embodiments, the magnitude, rate and duration of therapeutic induction of relative bradycardia may be based on any of several heart rate fiducial values, including: a) the patient's maximum heart rate according to either a formula (e.g., 220–age in years) or by patient-specific stress testing, b) resting heart rate upon awakening but recumbent, c) resting heart rate while standing up still, etc., d) prevailing heart at the time of seizure onset (that may be similar or different from the resting heart rate), e) fitness level, f) presence, degree and extent of atherosclerotic disease, g) risk of injury at the time therapeutic bradycardia or hypotension are induced, or any other factors that may increase the probability or severity of adverse effects of the therapy.

In one embodiment, therapeutic decreases in systemic blood pressure using means known to those skilled in the art may replace or complement induction of bradycardia to prevent or block epileptic seizures.

The methods depicted in FIG. 3 and FIG. 4 and described above may be governed by instructions that are stored in a non-transitory computer readable storage medium and that are executed by, e.g., a processor 217 of the medical device 200. Each of the operations shown in FIG. 3 and FIG. 4 may correspond to instructions stored in a non-transitory computer memory or computer readable storage medium. In various embodiments, the non-transitory computer readable storage medium includes a magnetic or optical disk storage device, solid state storage devices such as flash memory, or other non-volatile memory device or devices. The computer readable instructions stored on the non-transitory computer readable storage medium may be in source code, assembly language code, object code, or other instruction format that is interpreted and/or executable by one or more processors.

What is claimed:

1. A non-transitory computer readable program storage unit encoded with instructions that, when executed by a computer, perform a method of treating an epileptic seizure in a patient, comprising:

detecting via one or more processors the epileptic seizure, based on body data from the patient; and reducing a blood pressure of the patient in response to the detected epileptic seizure; and stopping or modifying the reduction in blood pressure in response to an unsafe drop in blood pressure.

2. The non-transitory computer readable program storage unit of claim 1, wherein the reducing the blood pressure of the patient in response to the detected epileptic seizure further includes reducing the flow of blood to a brain of the patient.

3. The non-transitory computer readable program storage unit of claim 1, wherein an electrical stimulation is administered to at least a portion of a right vagus nerve or a branch thereof.

4. The non-transitory computer readable program storage unit of claim 1, further comprising the reduction of the blood pressure of the patient is further effected by increasing the parasympathetic input to the heart via delivering a cholinergic drug or a drug with sympatho-blocking actions.

5. The non-transitory computer readable program storage unit of claim 4, wherein said cholinergic drug or said drug with sympatho-blocking actions is delivered by a catheter attached to a drug delivery device.

6. The non-transitory computer readable program storage unit of claim 4, wherein the reducing is effected by the delivering the cholinergic agent or the sympatho-blocking agent.

7. The non-transitory computer readable program storage unit of claim 1, further comprising the reduction of the blood pressure of the patient is further effected by increasing the parasympathetic input to the heart via applying a cooling to a sympathetic nervous structure.

8. The non-transitory computer readable program storage unit of claim 7, wherein the cooling is applied by a thermoelectric device or a refrigerant system.

9. The non-transitory computer readable program storage unit of claim 1, further comprising stopping or modifying the blood pressure reduction in response to at least one of a) a termination of the epileptic seizure; b) an increase in power in a 0-4 Hz frequency band in at least one brain region; c) a decrease in power in all frequency bands in at least one brain region; d) an impairment of a neurological function in at least one brain region; e) a change in antigravitatory muscle tone outside a normal range; f) an input from the patient requesting a therapy be terminated or modified; g) a drop in heart rate or blood pressure greater than that which was pre-specified, or h) an overly prolonged or intense prevention of increases in heart rate or blood pressure.

10. The non-transitory computer readable program storage unit of claim 1, further comprising stopping or modifying the blood pressure reduction, in response to at least one of a patient input and an occurrence of an adverse therapy effect.

11. A non-transitory computer readable program storage unit encoded with instructions that, when executed by a computer, perform a method of treating an epileptic seizure in a patient, comprising:

detecting via one or more processors the epileptic seizure, based on body data from the patient; and decreasing a sympathetic input to a heart of the patient in response to the detected epileptic seizure; and stopping or modifying the decreased sympathetic input, in response to an unsafe drop in blood pressure.

12. The non-transitory computer readable program storage unit of claim 11, further comprising identifying an epileptogenic or pro-epileptogenic brain region, and wherein the body data is indicative of epileptogenic or pro-epileptogenic activity in the epileptogenic or pro-epileptogenic brain region.

13. The non-transitory computer readable program storage unit of claim 11, further comprising decreasing the sympathetic input to the heart via thermal blocking of the sympathetic nervous structure.

14. The non-transitory computer readable program storage unit of claim 13, wherein the thermal blocking is applied by a thermoelectric device or a refrigerant system.

15. The non-transitory computer readable program storage unit of claim 11, further comprising stopping or modifying the electrical stimulation, in response to at least one of a) a termination of the epileptic seizure; b) an increase in power in a 0-4 Hz frequency band in at least one brain region; c) a decrease in power in all frequency bands in at least one brain region; d) an impairment of a neurological function in at least one brain region; e) a change in antigravitatory muscle tone outside a normal range; f) an input from the patient requesting a therapy be terminated or modified; g) a drop in heart rate or blood pressure greater than that which was pre-specified, or h) an overly prolonged or intense prevention of increases in heart rate or blood pressure.

16. The non-transitory computer readable program storage unit of claim 11, further comprising performing an action in response to detecting the epileptic seizure, wherein the action comprises at least one of:

providing a second therapy different from reducing a flow of blood to a brain;

logging at least one of detecting the epileptic seizure, an environmental circumstance associated with the epileptic seizure, at least one effect of a therapy or an action taken in response to the epileptic seizure; or providing a warning of detecting the epileptic seizure or if at least one adverse effect occurs.

17. The non-transitory computer readable program storage unit of claim 16, wherein providing the warning comprises at least one of an audible warning, a mechanical warning, or an electronic warning.

18. The non-transitory computer readable program storage unit of claim 16, wherein providing the second therapy comprises providing at least one of an electrical therapy, a thermal therapy, or a chemical therapy.

19. The non-transitory computer readable program storage unit of claim 11, wherein stopping or modifying the administering is further based on an unsafe change in heart rate.

* * * * *